(12) United States Patent
Fried

(10) Patent No.: US 11,207,490 B1
(45) Date of Patent: Dec. 28, 2021

(54) SENSORY CONTROL HEADGEAR AND METHOD OF USE

(71) Applicant: Scott Fried, Gwynedd Valley, PA (US)

(72) Inventor: Scott Fried, Gwynedd Valley, PA (US)

(*) Notice: Subject to any disclaimer, the term of this patent is extended or adjusted under 35 U.S.C. 154(b) by 384 days.

(21) Appl. No.: 16/290,052

(22) Filed: Mar. 1, 2019

Related U.S. Application Data

(60) Provisional application No. 62/775,120, filed on Dec. 4, 2018.

(51) Int. Cl.
*A61M 21/02* (2006.01)
*A61F 9/04* (2006.01)
*A61N 5/06* (2006.01)
*A61M 21/00* (2006.01)

(52) U.S. Cl.
CPC ............... *A61M 21/02* (2013.01); *A61F 9/04* (2013.01); *A61M 2021/005* (2013.01); *A61M 2021/0027* (2013.01); *A61N 5/0618* (2013.01)

(58) Field of Classification Search
CPC ..................... A61M 2021/0044; A61M 21/00
See application file for complete search history.

(56) References Cited

U.S. PATENT DOCUMENTS 4,520,510 A * 6/1985 Daigle .................... A61F 9/029
    2/12
6,319,015 B1 * 11/2001 Faunce .................. H01R 11/22
    24/662

* cited by examiner

*Primary Examiner* — Christine H Matthews
(74) *Attorney, Agent, or Firm* — Garcia-Zamor Intellectual Property Law, LLC; Ruy Garcia-Zamor

(57) ABSTRACT

Sensory control headgear which may provide therapeutic benefits by promoting relaxation, improve sleep, snoring reduction or prevention, anxiety control, stress relief, personal growth and motivation, study and learning preparedness, assisting with childbirth, pain control or reduction, relaxation and comfort with surgery, etc.

15 Claims, 15 Drawing Sheets

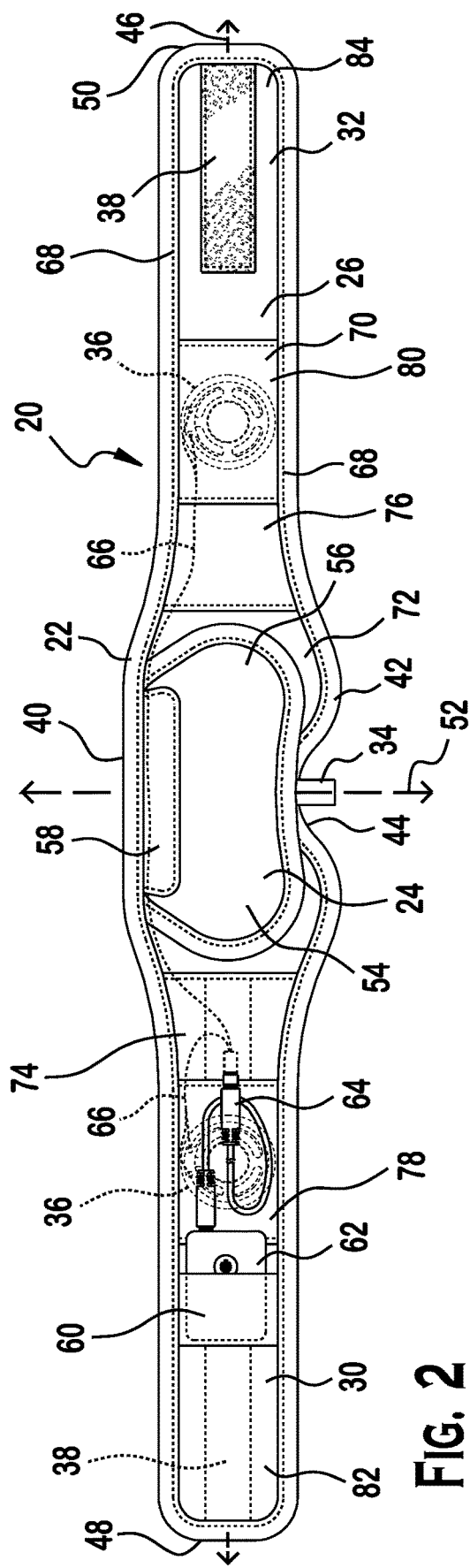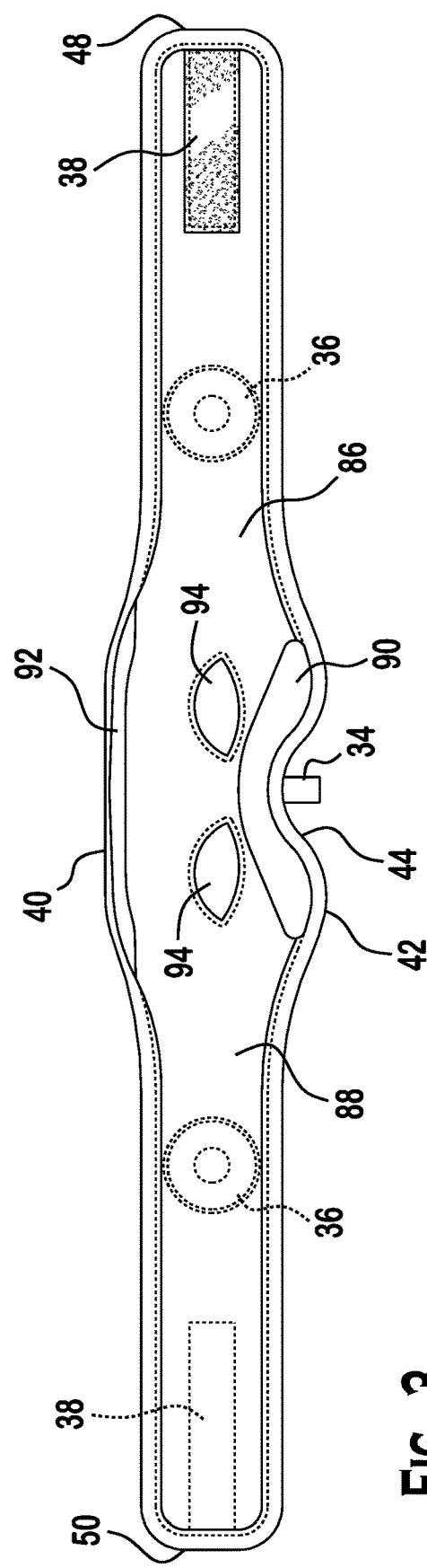

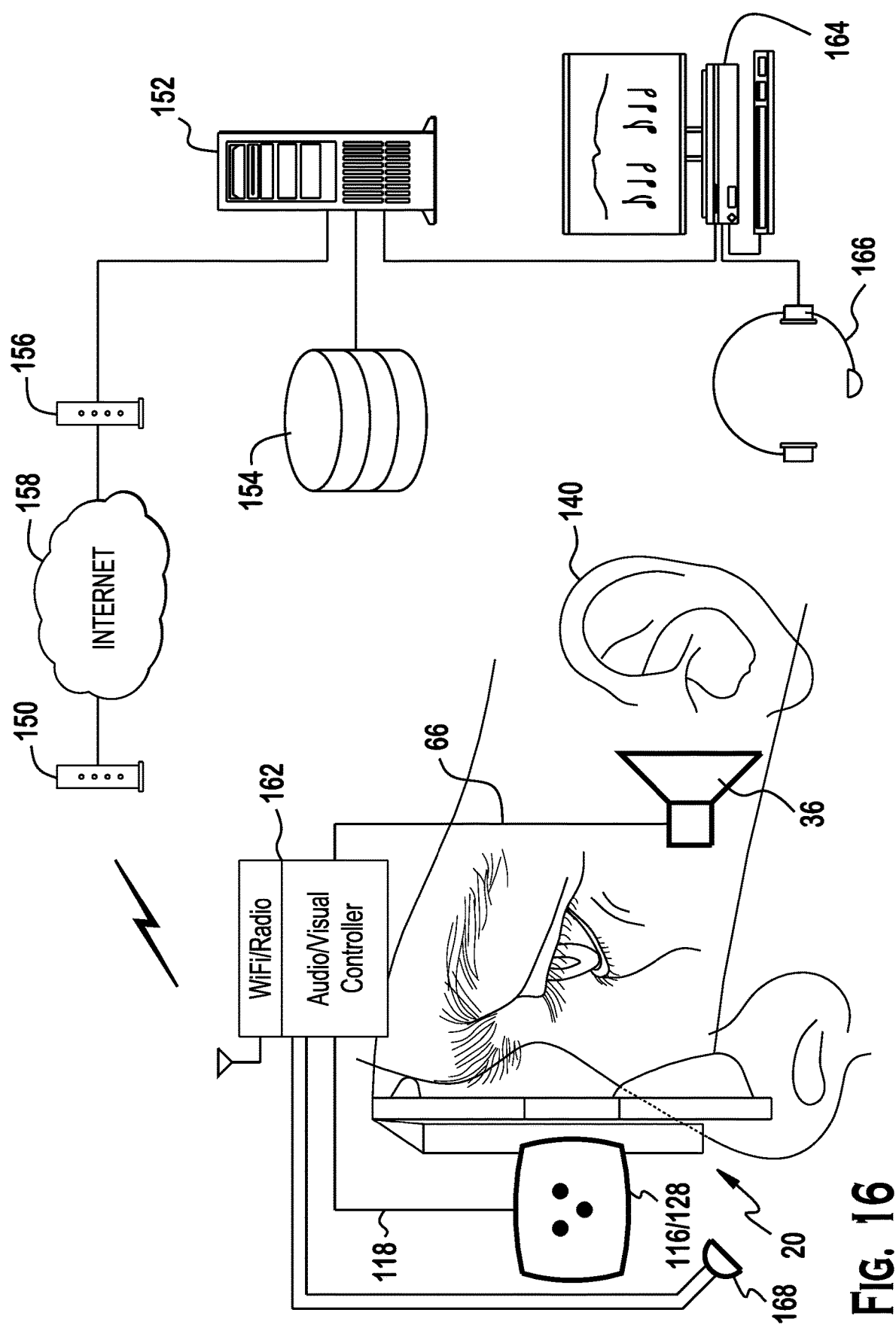

SENSORY CONTROL HEADGEAR AND METHOD OF USE

CROSS REFERENCE TO RELATED APPLICATIONS

This application claims priority to and benefit of U.S. provisional patent application 62/775,120, filed Dec. 4, 2018, which is hereby incorporated by reference in its entirety as if fully set forth herein.

BACKGROUND

The present invention relates generally to devices used for sensory modulation. It is more preferred that the present invention relate to devices and systems which allow a user to customize sensory input.

People often find it difficult to reduce surrounding stimuli when trying to relax, induce sleep, listen to an audio presentation, entering into a hypnotic or meditative state. This inability to control stimuli can lead to increased stress and frustration and negatively impact health.

It may be advantageous to provide sensory control headgear and/or a system for sensory control which preferably incorporates or makes possible at least one of: increasing the ability to relax; reduces and/or eliminates external stimuli; can deliver selected audio stimuli; can deliver selected visual stimuli; is made largely of soft fabric-type material; is easily operated by a user; allows remote assistance from third parties in achieving desired results; is enjoyable to use; and/or is preferably efficient to manufacture.

SUMMARY

In one aspect, the present invention is directed to a sensory control headgear configured for placement over a portion of a head of a user which includes a mask body. The mask body defines a central body portion and first and second lateral body portions configured for placement over eyes and ears of the user. The mask body is configured to reduce external noise perceived by the user. The mask body has a rear side configured to contact the head of the user when worn and a front side. The mask body defines a plurality of eye holes in the central body portion. The first and second lateral body portions are detachably securable to each other such that the sensory control headgear may be positioned about the head of the user. The mask body is preferably formed entirely of flexible fabric material. An eye shield is pivotably attached to the mask body for movement between a first, open position in which the user can see external surroundings through the plurality of eye holes in the mask body while the sensory control headgear is worn and a second, closed position in which external visual stimulation, or external stimuli, may be partially blocked or eliminated for the user while the sensory control headgear is worn. The mask body and the eye shield are configured such that pressure is not exerted onto the eyes of the user while the sensory control headgear is worn.

In another aspect, the present invention is directed to a sensory control headgear configured for placement over a portion of a head of a user. The sensory control headgear includes a mask body which defines a central body portion and first and second lateral body portions configured for placement over eyes and ears of the user. The mask body is configured to reduce external noise perceived by the user. The mask body has a rear side configured to contact the head of the user when worn and a front side. The mask body defines a plurality of eye holes in the central body portion. The first and second lateral body portions are detachably securable to each other such that the sensory control headgear is positioned about the head of the user. The mask body is formed entirely of flexible fabric material. An eye shield is pivotably attached to the mask body for movement between a first, open position in which the user can see external surroundings through the plurality of eye holes in the mask body while the sensory control headgear is worn and a second, closed position in which external visual stimulation is eliminated for the user while the sensory control headgear is worn. The mask body and the eye shield are configured such that pressure is not exerted onto the eyes of the user while the sensory control headgear is worn. A first ridge protuberance is positioned on the rear side of the mask body and configured to abut a nose of the user. A second ridge protuberance is positioned on the rear side of the mask body and configured to abut a forehead of the user such that the mask body is supported in a spaced apart fashion from the head of the user between the first ridge protuberance and the second ridge protuberance when the sensory control headgear is worn.

In another aspect, the present invention is directed to a sensory control headgear configured for placement over a portion of a head of a user. The sensory control headgear includes a mask body which defines a central body portion and first and second lateral body portions configured for placement over eyes and ears of the user. The mask body is configured to reduce external noise perceived by the user. The mask body has a rear side configured to contact the head of the user when worn and a front side. The mask body defines a plurality of eye holes in the central body portion. The first and second lateral body portions are detachably securable to each other such that the sensory control headgear is positioned about the head of the user. The mask body is formed entirely of flexible fabric material. An eye shield is pivotably attached to the mask body for movement between a first, open position in which the user can see external surroundings through the plurality of eye holes in the mask body while the sensory control headgear is worn and a second, closed position in which external visual stimulation is eliminated for the user while the sensory control headgear is worn. The eye shield is formed entirely of flexible fabric material. The mask body and the eye shield are configured such that pressure is not exerted onto the eyes of the user while the sensory control headgear is worn. A first ridge protuberance is positioned on the rear side of the mask body and configured to abut a nose of the user. A second ridge protuberance is positioned on the rear side of the mask body and configured to abut a forehead of the user such that the mask body is supported in a spaced apart fashion from the head of the user between the first ridge protuberance and the second ridge protuberance when the sensory control headgear is worn.

In another aspect, the present invention is directed to a sensory control headgear configured for placement over a portion of a head of a user. The sensory control headgear includes a mask body which defines a central body portion and first and second lateral body portions configured for placement over eyes of the user. The mask body has a rear side, configured to contact the head of the user when worn, and a front side. The mask body defines a plurality of eye holes in the central body portion. The first and second lateral body portions are detachably securable to each other such that the sensory control headgear can be positioned and held about the head of the user. The mask body is preferably formed entirely of flexible fabric material. An eye shield is pivotably attached to the mask body for movement between a first, open position in which the user can see external surroundings through the plurality of eye holes in the mask body while the sensory control headgear is worn; and a second, closed position, in which external visual stimuli is fully or partially blocked from the user's view while the sensory control headgear is worn. The mask body and the eye shield are configured such that pressure is not exerted onto the eyes of the user while the sensory control headgear is worn. A first ridge protuberance is positioned on the rear side of the mask body and configured to abut a nose of the user. A second ridge protuberance is positioned on the rear side of the mask body and configured to abut a forehead of the user such that the mask body is supported in a spaced apart fashion from the head of the user between the first ridge protuberance and the second ridge protuberance when the sensory control headgear is worn.

In another aspect, the present invention is directed to a sensory control headgear configured for placement over a portion of a head of a user. The sensory control headgear includes a mask body which defines a central body portion and first and second lateral body portions configured for placement over eyes of the user. The mask body has a rear side configured to contact the head of the user when worn, and a front side. The mask body defines a plurality of eye holes in the central body portion. An eye shield is pivotably attached to the mask body for movement between a first, open position in which the user can see external surroundings through the plurality of eye holes in the mask body while the sensory control headgear is worn; and a second, closed position, in which external visual stimuli is fully or partially blocked from the user's view while the sensory control headgear is worn. The mask body and the eye shield are configured such that pressure is not exerted onto the eyes of the user while the sensory control headgear is worn. A first ridge protuberance is positioned on the rear side of the mask body and configured to abut a nose of the user. A second ridge protuberance is positioned on the rear side of the mask body and configured to abut a forehead of the user such that the mask body is supported in a spaced apart fashion from the head of the user between the first ridge protuberance and the second ridge protuberance when the sensory control headgear is worn.

In another aspect, the present invention is directed to a sensory control headgear configured for placement over a portion of a head of a user. The sensory control headgear includes a mask body which defines a central body portion and first and second lateral body portions configured for placement over eyes of the user. The mask body has a rear side configured to contact the head of the user when worn and a front side. The mask body defines a plurality of eye holes in the central body portion. An eye shield is pivotably attached to the mask body for movement between a first, open position in which the user can see external surroundings through the plurality of eye holes in the mask body while the sensory control headgear is worn; and a second, closed position, in which external visual stimuli is fully or partially blocked from the user's view while the sensory control headgear is worn. The mask body and the eye shield are configured such that pressure is not exerted onto the eyes of the user while the sensory control headgear is worn.

In another aspect, the present invention is directed to a sensory control headgear configured for placement over a portion of a head of a user. The sensory control headgear includes a mask body which defines a central body portion and first and second lateral body portions configured for placement over eyes of the user. The mask body has a rear side configured to contact the head of the user when worn and a front side. The mask body defines a plurality of eye holes in the central body portion. An eye shield is pivotably attached to the mask body for movement between a first, open position in which the user can see external surroundings through the plurality of eye holes in the mask body while the sensory control headgear is worn; and a second, closed position, in which external visual stimuli is fully or partially blocked from the user's view while the sensory control headgear is worn.

In another aspect, the present invention is directed to a sensory control headgear configured for placement over a portion of a head of a user. The sensory control headgear includes a mask body which has a rear side, configured to contact the head of the user when worn, and a front side. The mask body defines a plurality of eye holes in the central body portion. An eye shield is pivotably attached to the mask body. The mask body and the eye shield are configured such that pressure is not exerted onto the eyes of the user while the sensory control headgear is worn.

BRIEF DESCRIPTION OF THE DRAWINGS

The foregoing summary, as well as the following detailed description of the preferred embodiments of the invention, will be better understood when read in conjunction with the appended drawings. For the purpose of illustrating the invention, there are shown in the drawings embodiments which are presently preferred. It is understood, however, that the invention is not limited to the precise arrangements and instrumentalities shown. In the drawings:

FIG. 2 is a front elevational view of the sensory control headgear 20 of FIG. 1. The sensory control headgear 20 includes a mask body 22 that is preferably generally elongated to extend along an axial axis 46. The mask body 22 may include a central portion 28 and first and second lateral portions 30, 32. The mask body 22 preferably includes a central panel 72, first and second transition panels 74, 76, first and second ear cover panels 78, 80, and first and second end panels 82, 84. The mask body 22 is preferably elongated with first and second axial ends 48, 50. An eye shield 24 is preferably located on the front side 26 of the mask body 22 and is generally pivotable around a top edge 40 of the mask body 22. A reinforcement section 58 may be included to bias the eye shield 24 into the second, closed position (as shown in FIG. 2).

FIG. 3 is a rear elevational view of the sensory control headgear 20 of FIG. 1. The mask body 22 preferably includes a liner 88 which extends along a majority of the rear side to increase the comfort of wearing the headgear for a user. Speakers 36 may be positioned within the mask body 22 to provide predetermined audio stimulation. Hook-and-loop material 38, or any suitable fastener, may be used to fasten the first and second lateral body portions 30, 32 of the mask body 20 together. As can be seen in the drawings, it is preferable that the mask body 22 is formed entirely of flexible fabric material that may be stitched 38 together. The mask body 22 preferably defines a plurality of eye holes 94 in the central body portion 28. As shown in the top of the figure, a first ridge protuberance 90 may be positioned on the rear side of the mask body 22 and configured to abut a nose of the user. A second ridge protuberance 92 may be positioned on the rear side of the mask body and configured to abut a forehead of the user.

FIG. 16 is a schematic diagram for a system for sensory control which includes the sensory control headgear 20 which is similar to that shown in FIG. 15. This system preferably includes a remotely located computer 164 and headset 166 for use by a trainer. The sensory control headgear 20 preferably includes a microphone 168 to allow for two-way audible communication with the trainer. The trainer can use the headset 166 and the computer display to guide the headgear where are through specific sensory input. This can be used to facilitate meditation, hypnosis, self-healing, etc.

DETAILED DESCRIPTION OF THE PREFERRED EMBODIMENTS

Figure 1:
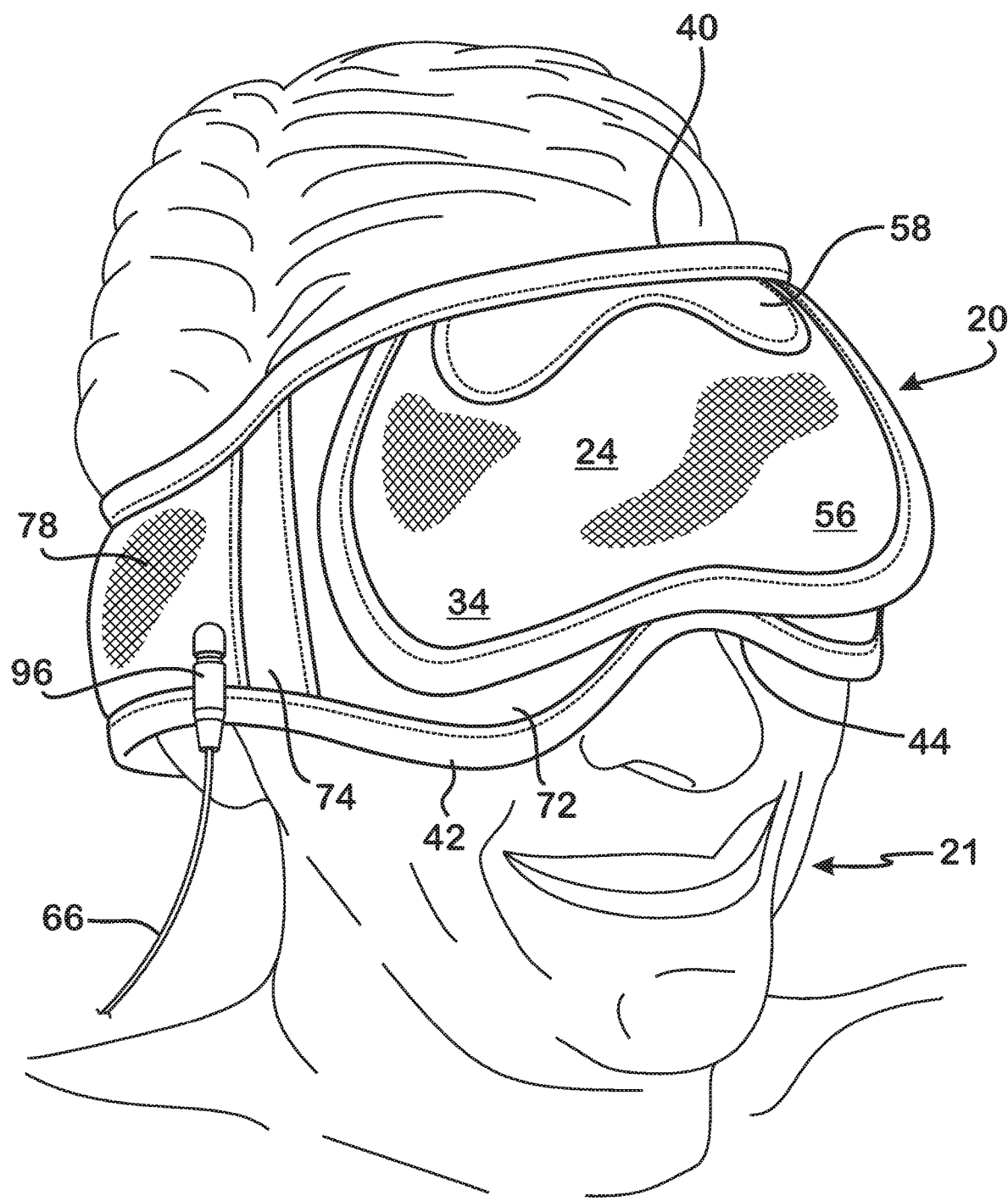
FIG. 1 is a front perspective view of the user 21 wearing sensory control headgear 20. The sensory control headgear 20 is preferably positioned on the face of the user 21 and is positioned generally along the cheeks and nose of the user and along the forehead of the user 21.

Certain terminology is used in the following description for convenience only and is not limiting. The words "right," "left," "top," and "bottom" designate directions in the drawings to which reference is made. Additionally, the words "a" and "one" are defined as including one or more of the referenced items unless specifically stated otherwise. The terminology includes the words above specifically mentioned, derivatives thereof, and words of similar import.

Referring to FIGS. 1-16, wherein like numerals indicate like elements throughout, preferred embodiments of a sensory control headgear according to the present invention are shown and generally designated as 20. It is preferred that the sensory control headgear 20 provide sensory visual and audio isolation from the surrounding environment while allowing preselected audio (and/or video) stimulus to be received. The mask body 22 is preferably efficiently designed to block out light and may incorporate speakers 36 to allow a user to listen of various presentations, such as how to reach one's goals, exercise motivation, relaxation, etc. The sensory control headgear 20 may provide therapeutic benefits by promoting relaxation, improving sleep, reducing or preventing snoring, controlling anxiety, assisting with stress relief, facilitating personal growth including motivation for studying and learning, assisting with pain control and childbirth, promoting relaxation and comfort with surgery, etc. Referring to FIGS. 13-16, the sensory control headgear 20 can be part of a system which may include remote servers 152 with podcasts or other downloadable presentations that may be prepared by professionals from across the spectrum, such as teachers, hypnosis society professionals, healers, yogis, mindfulness leaders, motivators, etc. The sensory control headgear 20 preferably makes it possible for the user to be placed in the perfect environment to achieve a particular mindset and to more quickly induce a hypnotic state. The mask body 22 facilitates the wearer being guided or instructed in how to enter a trance and then to guide the wearer's mind toward the desired result/goal. While visual isolation from the environment (or reduction in environmental stimulus) may be preferable, the sensory control headgear 20 may be enhanced with lights, video, and/or sound to allow customized audio content and customized visual content to be experienced which are separate from external stimulus. This can be ideal in soothing the wearer and promoting a reduction in stress.

Referring still to FIG. 1, a user 21 is shown wearing the sensory control headgear 20. The sensory control headgear 20 is preferably positioned on the face of the user 21 and is positioned generally along the cheeks and nose of the user and along the forehead of the user 21. The sensory control headgear 20 is preferably configured for placement over a portion of a head of a user 21.

Referring to FIGS. 2 and 3, the mask body 22 preferably defines a central body portion 28 and first and second lateral body portions 30, 32 configured for placement over eyes and ears of the user. The mask body 22 is preferably configured to reduce external noise perceived by the user. The mask body 22 has a rear side configured to contact the head of the user 21 when worn, and a front side 26. The mask body 22 defines a plurality of eye holes 94 in the central body portion 28. The first and second lateral body portions 30, 32 are preferably detachably securable to each other such that the sensory control headgear 20 may be positioned and held about the head of the user 21. The mask body 22 is preferably formed entirely of flexible fabric material. Such fabric may include neoprene, knit fabric, woven fabric, or the like.

The sensory control headgear 20 preferably includes a mask body 22 that is preferably generally elongated to extend along an axial axis 46. The mask body 22 may include a central portion 28 and first and second lateral portions 30, 32. The mask body 22 preferably includes a central panel 72, first and second transition panels 74, 76, first and second ear cover panels 78, 80, and first and second end panels 82, 84. The mask body 22 is preferably elongated with first and second axial ends 48, 50. An eye shield 24 is preferably located on the front side 26 of the mask body 22 and is generally pivotable around a top edge 40 of the mask body 22. A reinforcement section 58 may be included to bias the eye shield 24 into the second, closed position (as shown in FIG. 2).

The mask body 22 preferably includes a liner 88 which extends along a majority of the rear side to increase the comfort of wearing the headgear for a user. The liner 88 may be felt, silk, or any other suitable material which may comfortably contact the user 21. Speakers 36 may be positioned within the mask body 22 to provide predetermined audio stimulation. Hook and loop material 38, or any suitable fastener, may be used to fasten the first and second lateral body portions 30, 32 of the mask body 20 together. As can be seen in the drawings, it is preferable that the mask body 22 is formed entirely of flexible fabric material that may be stitched 38 together. The mask body 22 preferably defines a plurality of eye holes 94 in the central body portion 28. As shown in the top of the figure, a first ridge protuberance 90 may be positioned on the rear side of the mask body 22 and configured to abut a nose of the user. A second ridge protuberance 92 may be positioned on the rear side of the mask body and configured to abut a forehead of the user.

The mask body 22 may be configured as a single elongated member such that a top of the head of the user 21 is not covered while the sensory control headgear 20 is worn. The mask body may be configured to contact the face of the user around all of each eye socket of the plurality of eyes so as to encircle each eye socket individually. This effectively provides miniature tubes, each around a single lie that preferably lie along the edge of the wearer's eye socket.

Figure 4:
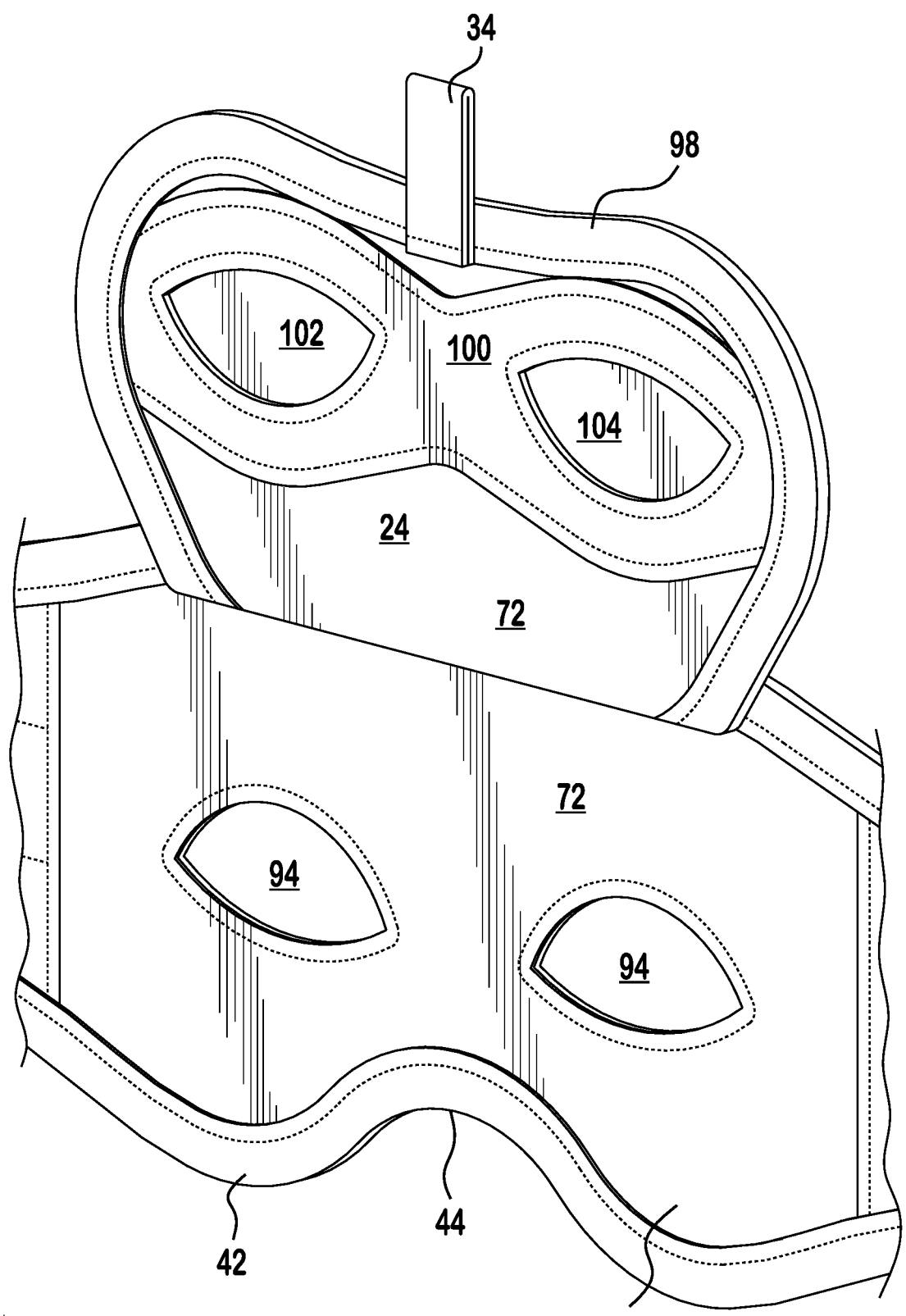
FIG. 4 is and the enlarged, broken away, front perspective view of the sensory control headgear 20 of FIG. 1. The eye shield 24 is shown pivoted into a first, open position in which the user can see external surroundings through the plurality of eyeholes 94 in the mask body 22 while the sensory control headgear 20 is worn. The eye shield 24 preferably includes a spacer 100 that is configured such that when the eye shield 24 is in the second, closed position the spacer 100 is positioned against the entire perimeter of each of the plurality of eye slots 94 in the mask body 22. A tab 34 may be located on the eye shield 24 to allow for simple movement of the eye shield 24 by the user.
Figure 5:
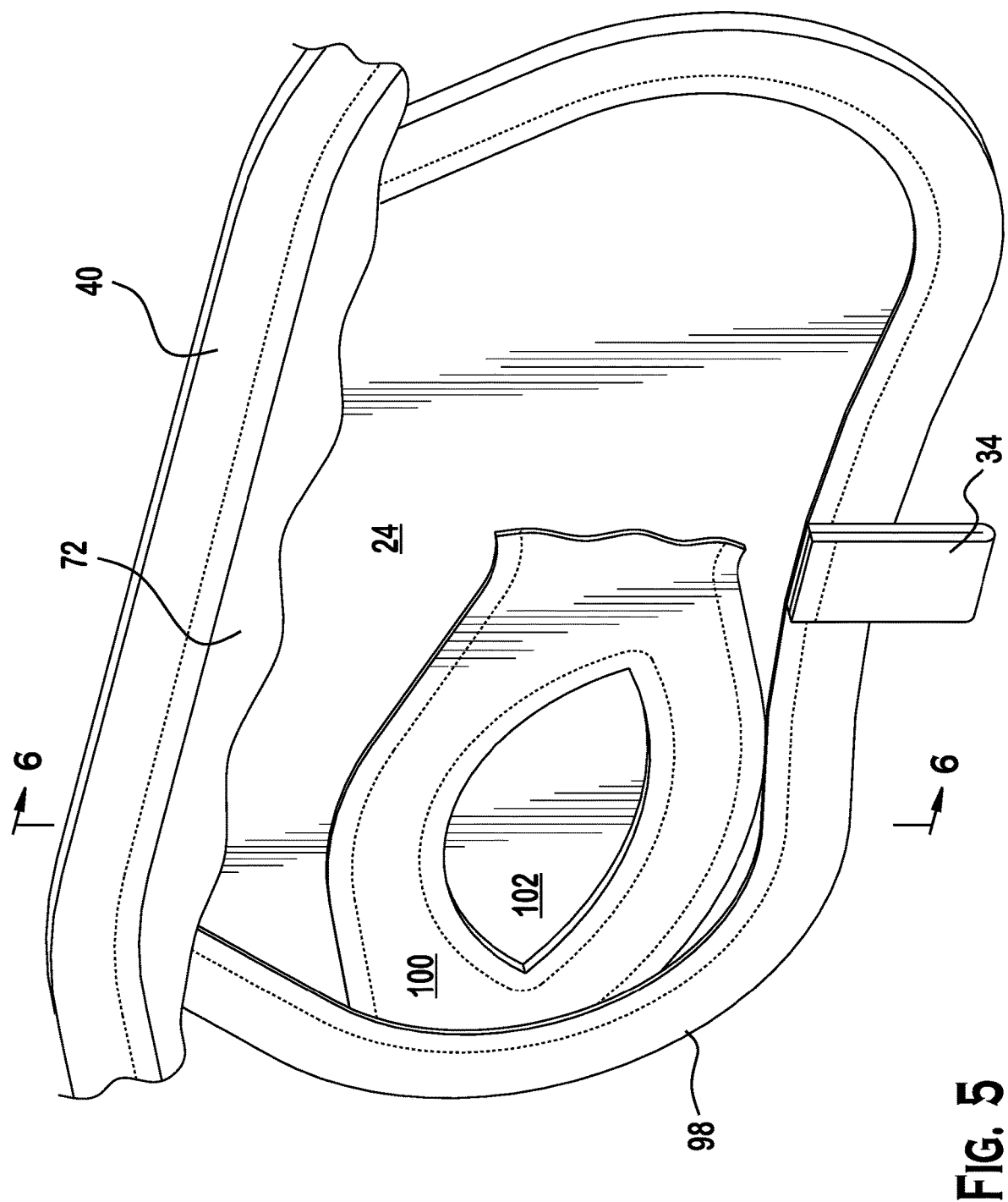
FIG. 5 is a partial, broken away, rear perspective view of the sensory control headgear 20 with the eye shield 24 in a second, closed position in which external visual stimulation is eliminated and/or reduced for the user while the sensory control headgear is worn. The mask body 22 is broken away to facilitate looking at the inner surface of the eye shield in the second, closed position. The spacer 100 is also broken away to illustrate its possible positioning by sewing the spacer 100 onto an inner surface of the eye shield 24. The spacer 100 preferably defines first and second cut outs 104 which preferably correspond to the plurality of eyeholes 94 and the mask body.
Figure 6:
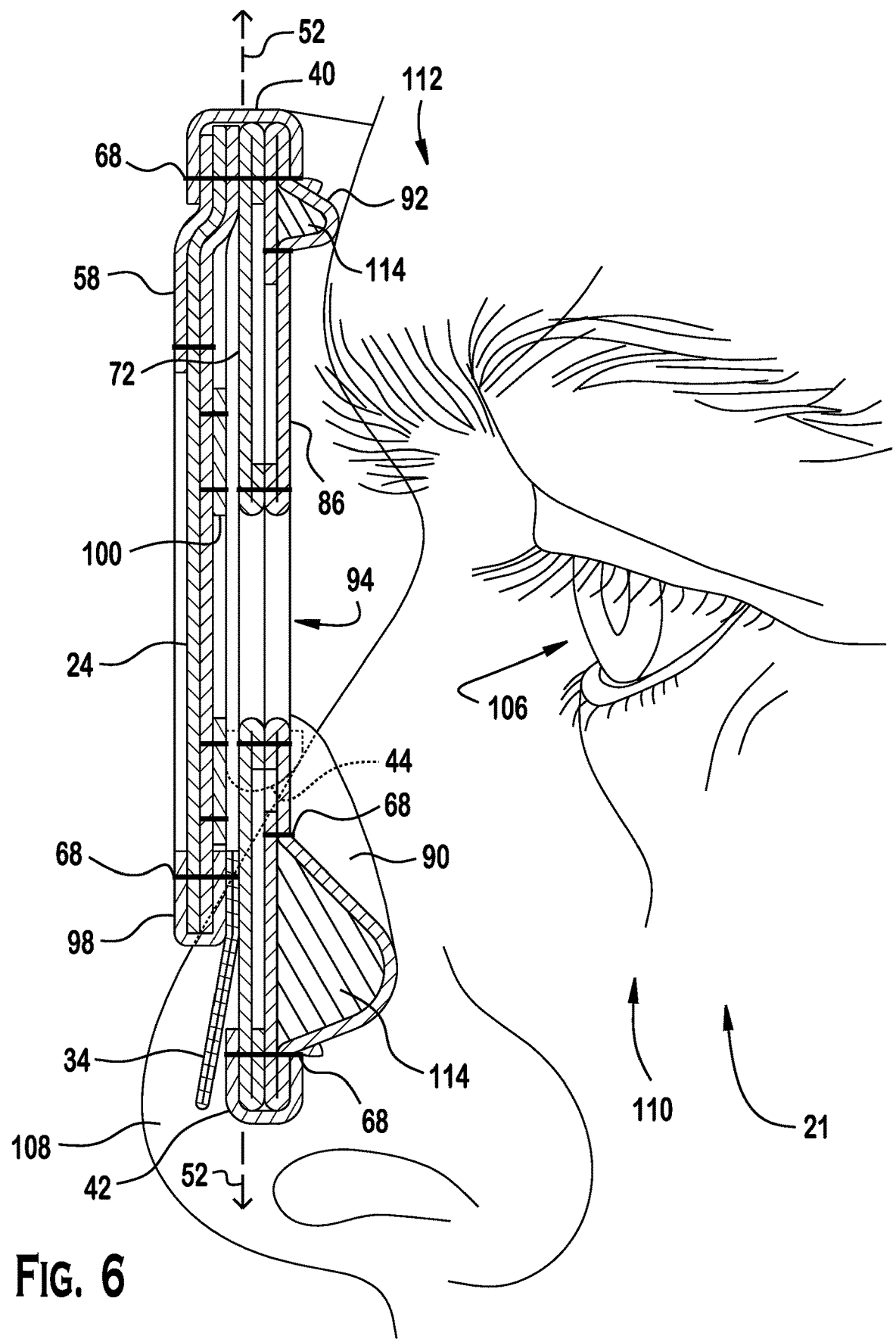
FIG. 6 is cross-sectional view of the sensory control headgear 20 of FIG. 5 as taken along the lines 6-6 in FIG. 5 while the sensory control headgear 20 is worn by a user 21. The sensory control headgear is preferably formed entirely from flexible fabric that is sewn together. However, those of ordinary skill in the art will appreciate from this disclosure that any suitable materials can be used without parting from the present invention. The first ridge protuberance which abuts a nose of the user and the second ridge protuberance 92 which abuts a forehead of the user may be configured such that the mask body 22 is supported in a spaced-apart fashion from the head (such that there is no contact) of the user between the first ridge protuberance 90 and the second ridge protuberance 92. The mask body 22 has sewn together layers which may be formed by the liner 86 and central panel 72. The eye shield 24 may be formed by layers of material to which a spacer 100 is shown.
Figure 7:
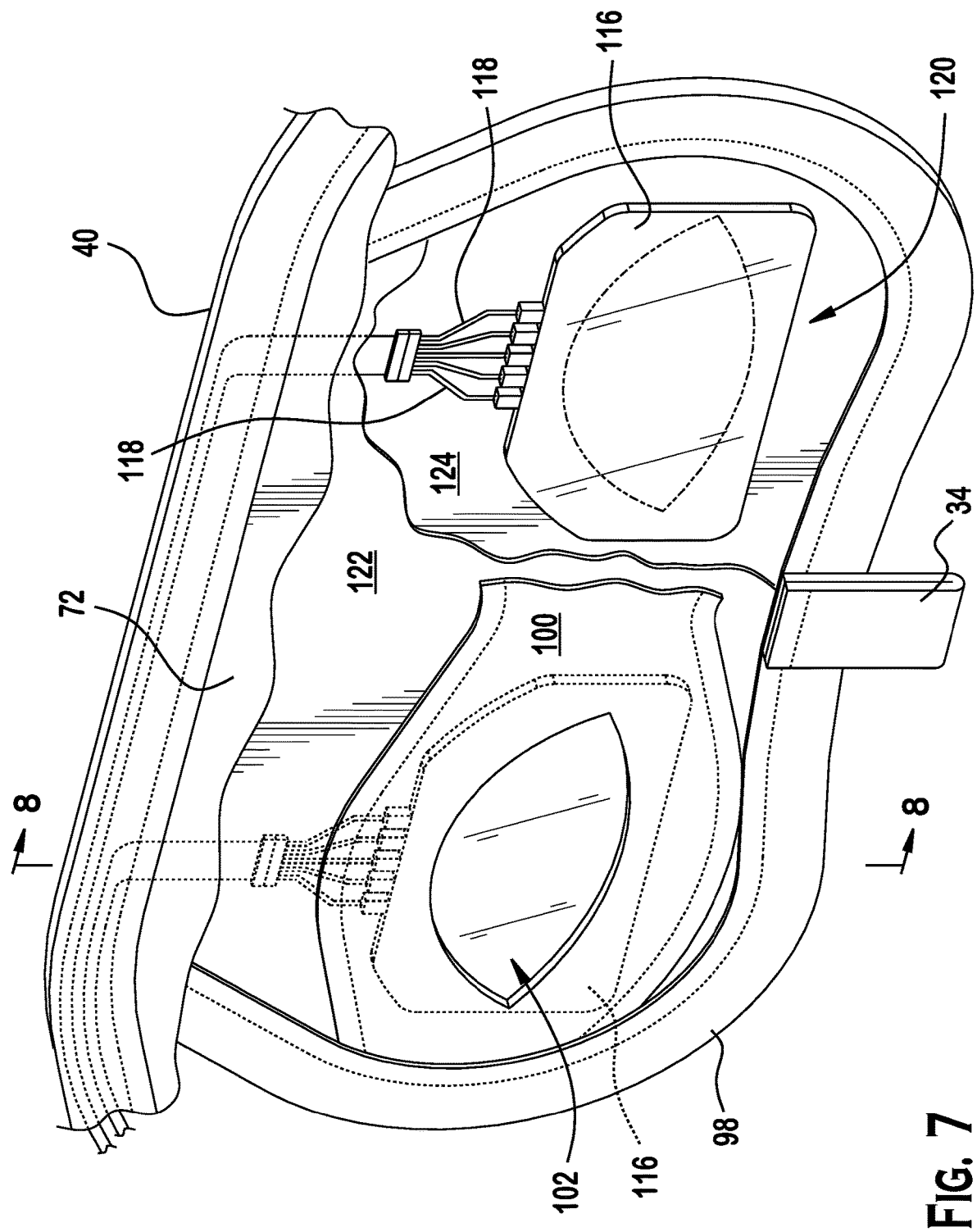
FIG. 7 is a partial, broken away, rear perspective view of an alternate embodiment of the sensory control headgear 20 similar to that shown in FIG. 5 with the eye shield 24 in a second, closed position in which external visual stimulation is eliminated and/or reduced for the user while the sensory control headgear is worn. An illuminated display 116 may be located between inner panel 122 and outer panel 124 of the eye shield 24 was cut outs 102 provided in the inner panel 122 so that a user can observe predetermined visual content. The illuminated display 116 may be illuminated glass, glass piping, a light pipe lens, a light display, a video display, a liquid crystal display, a light-emitting diode display, a multicolor light-emitting diode, and a light-emitting diode.

Referring to FIGS. 4-6, an eye shield 24 is preferably pivotably attached to the mask body 22 for movement between a first, open position (as shown in FIG. 4) in which the user 21 can see external surroundings through the plurality of eye holes 94 in the mask body 22 while the sensory control headgear 20 is worn; and a second, closed position (as shown in FIG. 7), in which external visual stimulation is preferably eliminated (or at least reduced) for the user 21 while the sensory control headgear 20 is worn.

The eye shield 24 preferably incudes a spacer 100 configured such that when the eye shield 24 is in the second, closed position, the spacer 100 is positioned against the entire perimeter of each of the plurality of eye slots in the mask body 22. Referring specifically to FIG. 4, the eye shield 24 is shown pivoted into a first, open position in which the user can see external surroundings through the plurality of eyeholes 94 in the mask body 22 while the sensory control headgear 20 is worn. The eye shield 24 preferably includes a spacer 100 that is configured such that when the eye shield 24 is in the second, closed position, the spacer 100 is positioned against the entire perimeter of each of the plurality of eye slots 94 in the mask body 22. A tab 34 may be located on the eye shield 24 to allow for simple movement of the eye shield 24 by the user.

Referring specifically to FIG. 5, the mask body 22 is broken away to facilitate looking at the inner surface of the eye shield in the second, closed position. The spacer 100 is also broken away to illustrate its possible positioning by sewing the spacer 100 onto an inner surface of the eye shield 24. The spacer 100 preferably defines first and second cut outs 104 which preferably correspond to the plurality of eyeholes 94 in the mask body.

Referring specifically to FIG. 6, the sensory control headgear 20 is preferably formed entirely from flexible fabric that is sewn together. However, those of ordinary skill in the art will appreciate from this disclosure that any suitable materials can be used without parting from the present invention. Additionally, those of ordinary skill in the art will appreciate from this disclosure that the materials of the sensory control headgear 20 may be secured together via adhesive, hot weld, sonic weld, or any other suitable method without departing from the scope of the present invention.

The first ridge protuberance 90, which preferably abuts a nose 108 of the user 21 and the second ridge protuberance 92, which preferably abuts a forehead 112 of the user 21, may be configured such that the mask body 22 is supported in a spaced apart fashion from the head of the user between the first ridge protuberance 90 and the second ridge protuberance 92. Alternatively, it may be preferable that there is no contact between the mask body 22 and the head of the user 21 between the first ridge protuberance 90 and the second ridge protuberance 92. The mask body 22 may be formed with sewn together layers which may be formed by the liner 86 and central panel 72. The eye shield 24 may be formed by layers of material to which a spacer 100 is shown.

The mask body and the eye shield are preferably configured such that pressure is not exerted onto the eyes of the user while the sensory control headgear 20 is worn. It is preferable that there is no contact between the mask body 22 and the eye shield 24 and the eyes or eyelids of the user. It is more preferable still that there is no contact between the mask body 22 and the eye shield 24 with the eyelashes of the user 21. This is made possible in some cases by the first and second ridge protuberances 90, 92 spacing the rear side of the mask body 22 away from a portion of the user's face.

Figure 8:
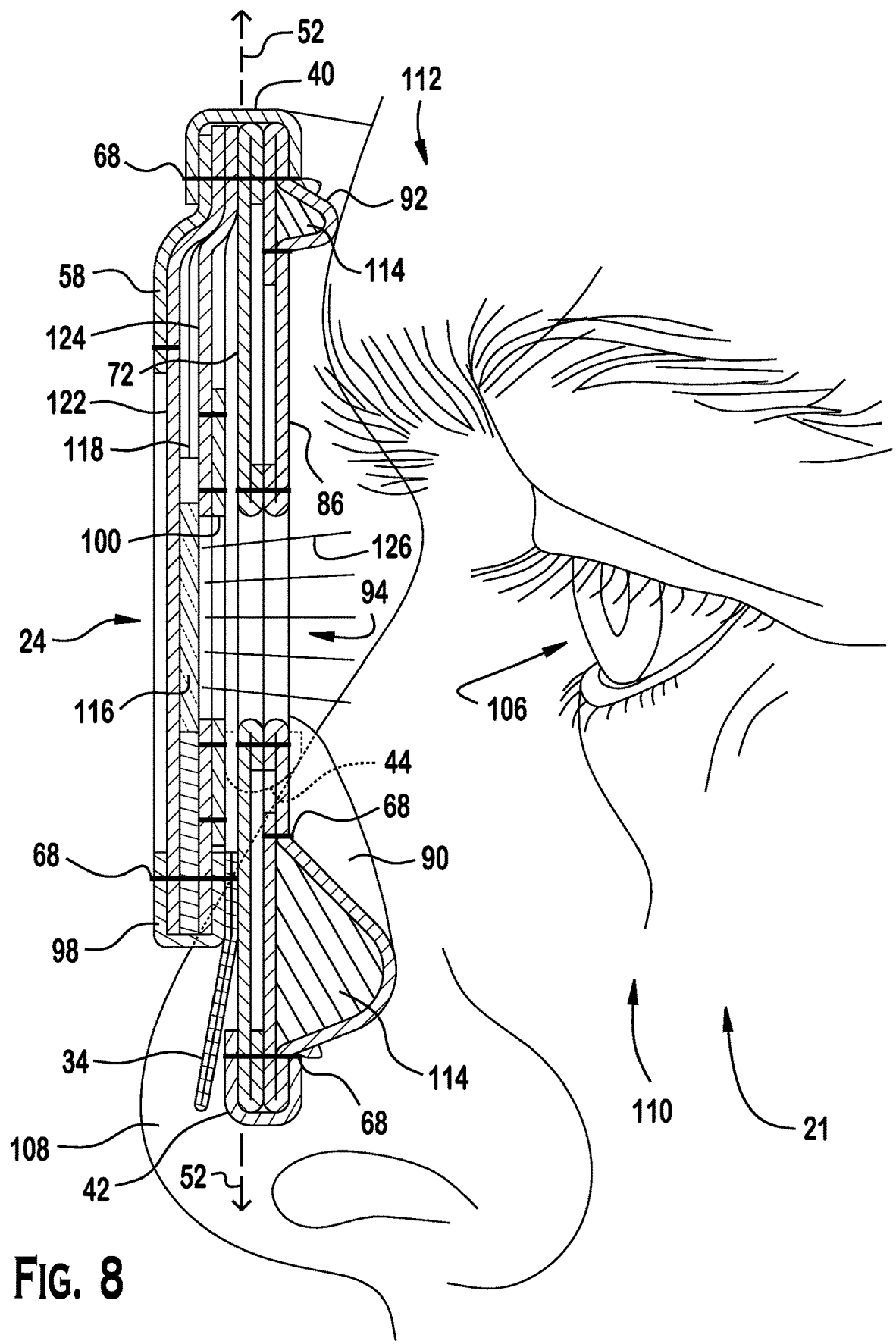
FIG. 8 is a cross-sectional view of the sensory control headgear 20 of FIG. 7 as taken along the lines 8-8 in FIG. 7 illustrating a user's viewing of illumination 126 received from the illumination panel 116. The illumination panel is shown positioned between the inner and outer panels 122, 124 of the eye shield 24. The user 21 can view the illumination 126 via the eyeholes 94 in the mask body 22 and via the cut outs 102 in the eye shield 24.
Figure 9:
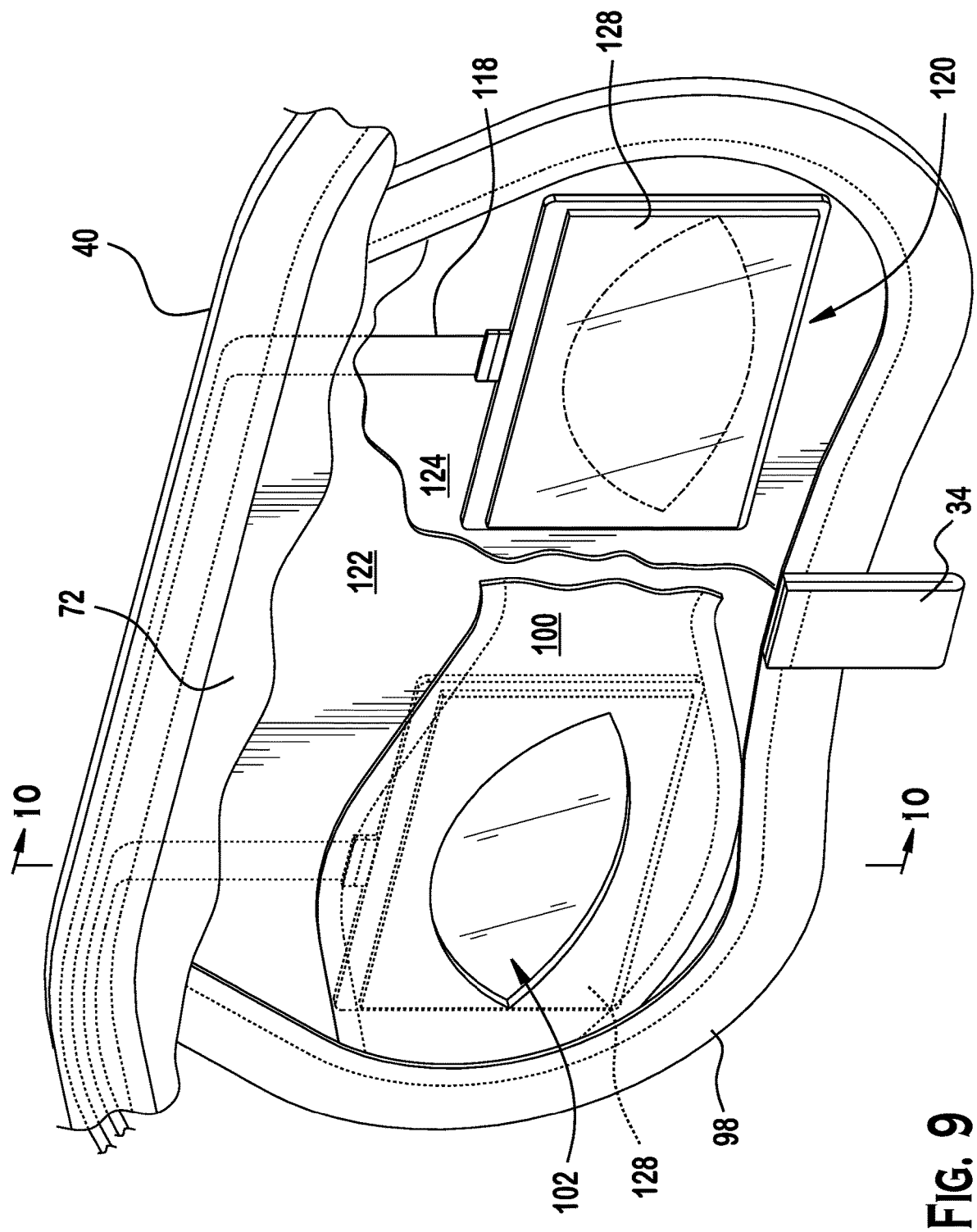
FIG. 9 is view similar to that of FIG. 7 in which the illumination panel is an LCD screen or other video display.
Figure 10:
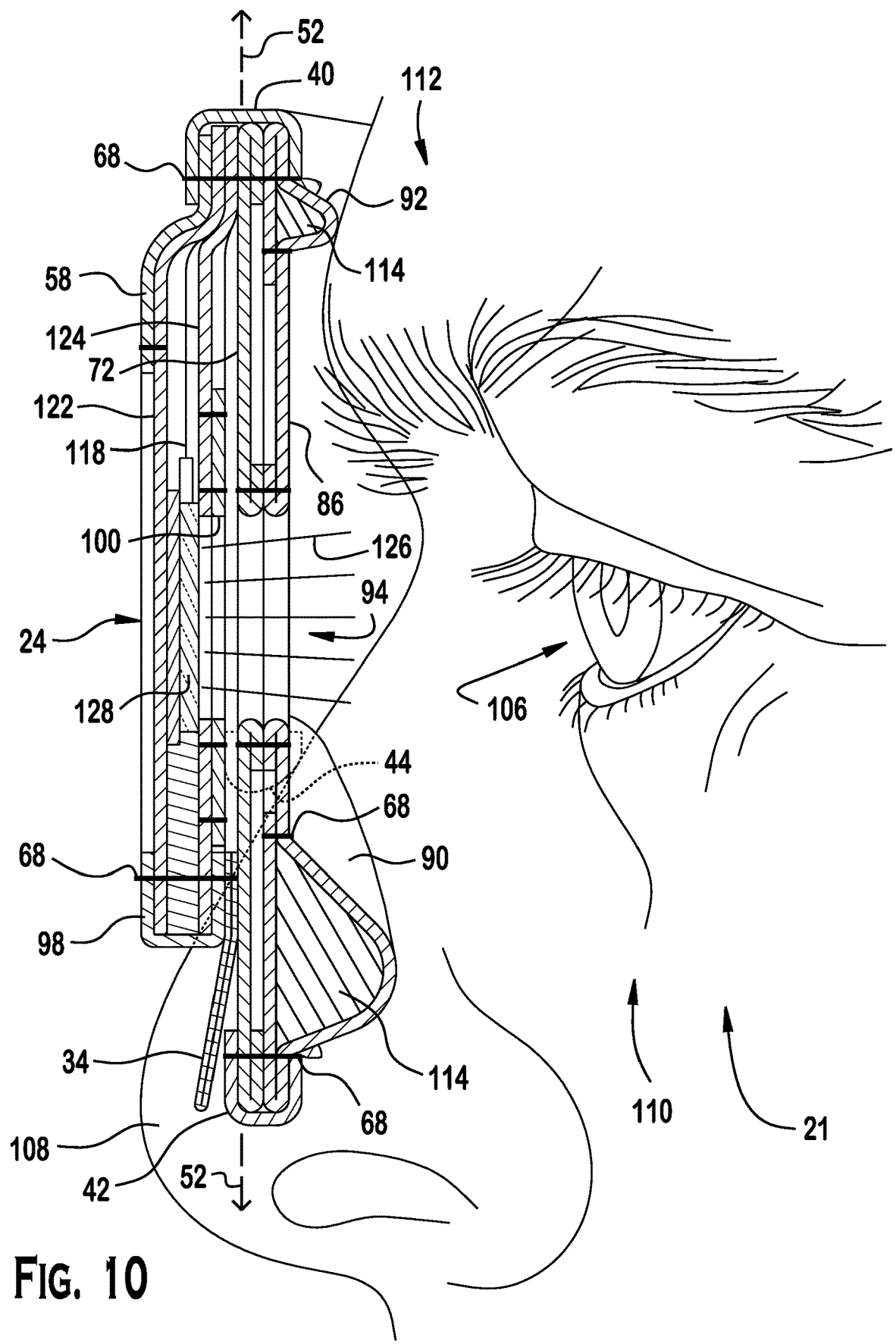
FIG. 10 is view similar to that of FIG. 8 in which the illumination panel is an LCD screen or other video display.
Figure 11:
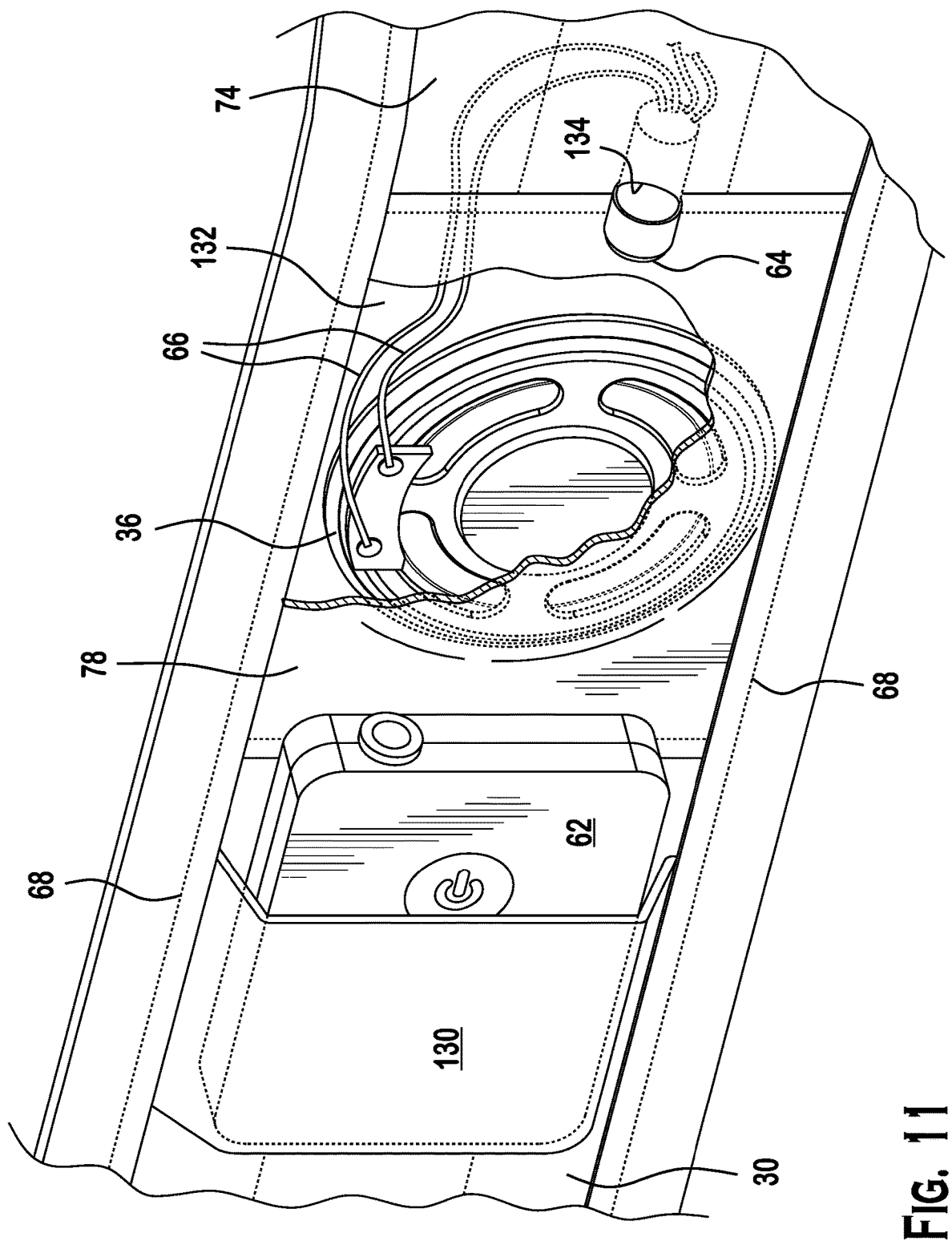
FIG. 11 is a partial broken away view of the mask body 22 showing a pocket 134 containing a digital playback device 62 and illustrating a speaker 36 located within a speaker enclosure one 32 within the mask body 22.

Referring to FIG. 8, the first ridge protuberance 90 is preferably positioned on the rear side of the mask body 22 and configured to abut a nose 108 of the user 21. The second ridge protuberance 92 is preferably positioned on the rear side of the mask body and configured to abut a forehead 112 of the user 21 such that the mask body is supported in a spaced apart fashion from the head of the user between the first ridge protuberance 90 and the second ridge protuberance 92. As shown in FIG. 8, it is possible that, in some embodiments of the present invention, the mask body 22 is sufficiently spaced from the user's face 110 such that not only do the eyes, eyelids, and eyelashes not contact the mask body 22, but the user's eyebrows do not contact the mask 22. It is preferred that the sensory control headgear 20 minimize external stimuli while maintaining maximum comfort and minimum distraction for the user.

Referring to FIGS. 7-12, the sensory control headgear 20 is preferably positionable with the eye shield 24 in a second, closed position, in which external visual stimulation is eliminated and/or reduced for the user while the sensory control headgear 20 is worn. An illuminated display 116 may be located between inner panel 122 and outer panel 124 of the eye shield 24. The inner panel 122 of the eye shield 24 may include cut outs 102 therethrough so that a user can observe predetermined visual content. The illuminated display 116, 128 may be illuminated glass, glass piping, a light pipe lens, a light display, a video display, a liquid crystal display, a light-emitting diode display, a multicolor light-emitting diode, and a light-emitting diode.

A user can preferably view illumination 126 received from the illumination panel 116. The illumination panel 116, 128 is preferably (but not necessarily) positioned between the inner and outer panels 122, 124 of the eye shield 24. The user 21 can view the illumination 126 via the eyeholes 94 in the mask body 22 and via the cut outs 102 in the eye shield 24.

The mask body 22 may include a pocket 134 containing a digital playback device 62. The speaker 36 may be located within a speaker enclosure 132 within the mask body 22.

Figure 12:
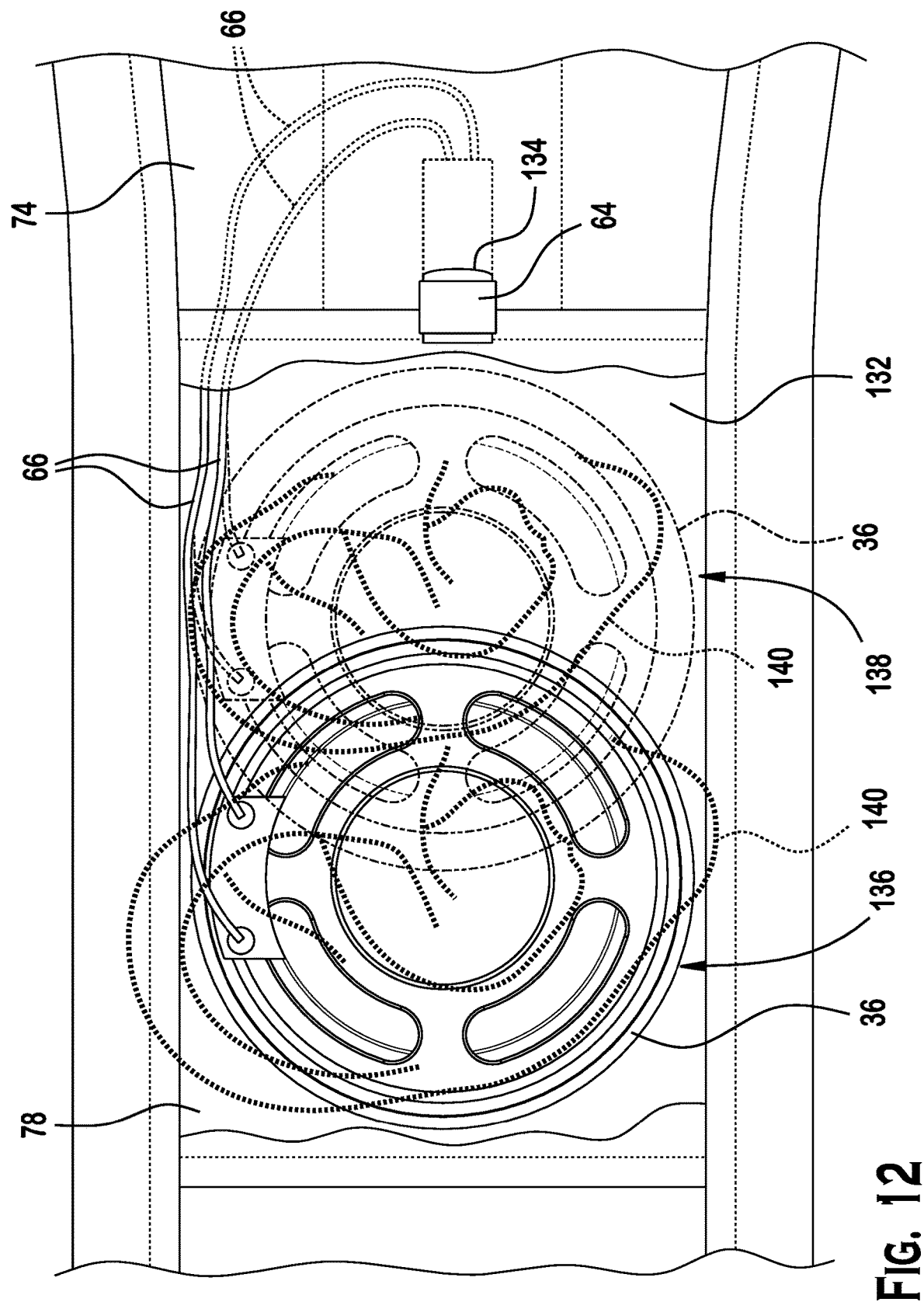
FIG. 12 is a view similar to that of FIG. 11 illustrating that it is preferred that the speakers 36 can be laterally slid within the speaker pocket between at least a first speaker position 136 and a second speaker position 138. This allows a user to optimally position speakers 36 for use while wearing the sensory control headgear 20.

Referring specifically to FIG. 12, it is preferred that the speakers 36 can be laterally slid within the speaker pocket between at least a first speaker position 136 and a second speaker position 138. This allows a user to optimally position speakers 36 for use while wearing the sensory control headgear 20.

The mask body 22 may include positioning the pocket on the front side thereof so that a digital source 62 can be positioned in the pocket 60 to provide at least one of the predetermined audio content and predetermined visual content. The digital source 62 which can provide podcast, MP3, MP4, audio, or visual content may be connected to the speaker 36 disposed within the mask body 22 to provide predetermined audio (and/or visual) content to the user. As mentioned above, the speaker 36 is preferably located within a chamber in the mask body 22 that allows the speaker to be moved axially between at least two positions.

Figure 13:
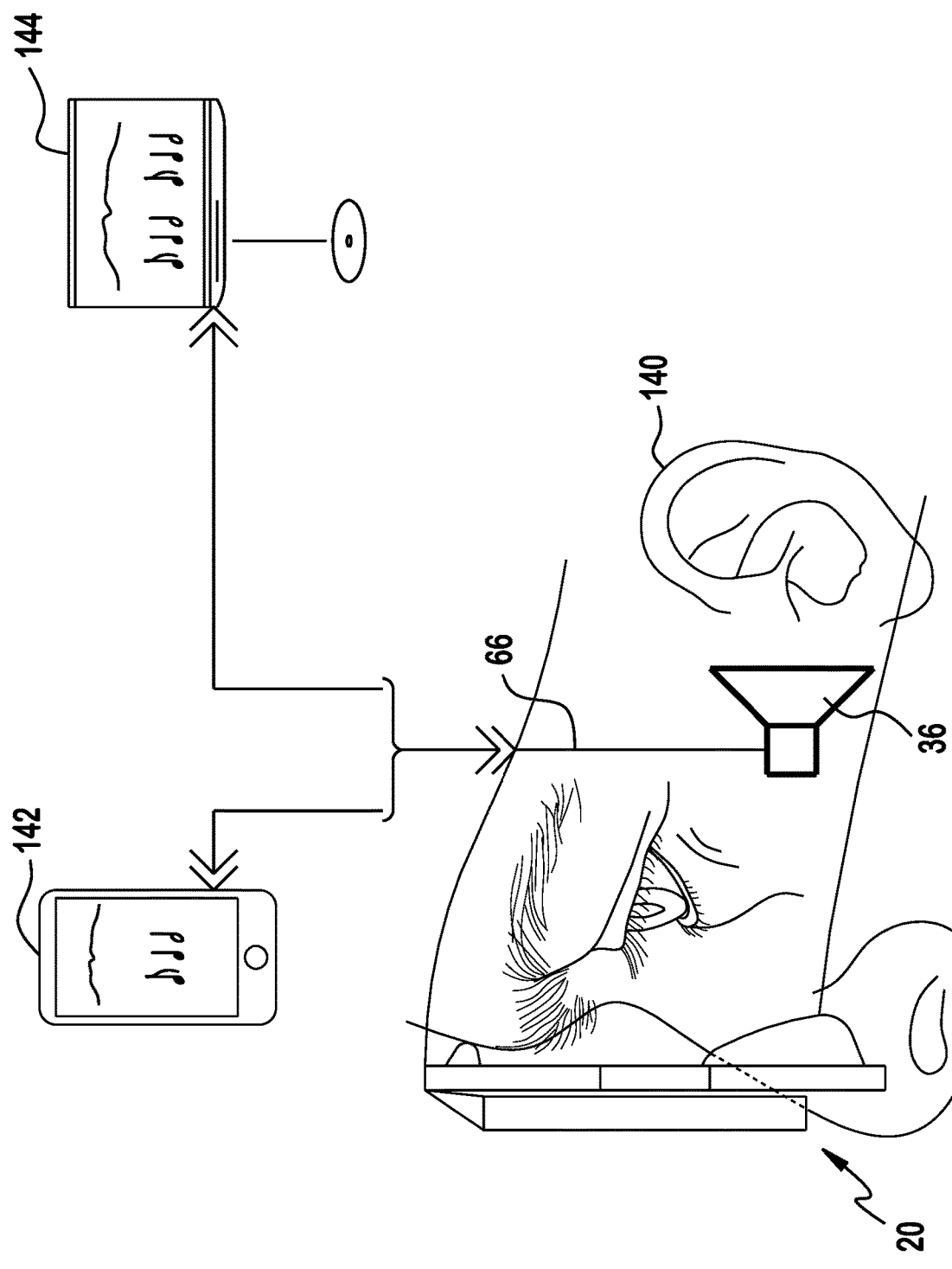
FIG. 13 a schematic diagram for a system for sensory control which preferably includes the sensory control headgear 20 of the present invention. The speaker 36 is preferably connected via adapters and wires 66 two mobile phones and such were mobile electronic devices 142 and computers, including tablets and laptops, 144.
Figure 14:
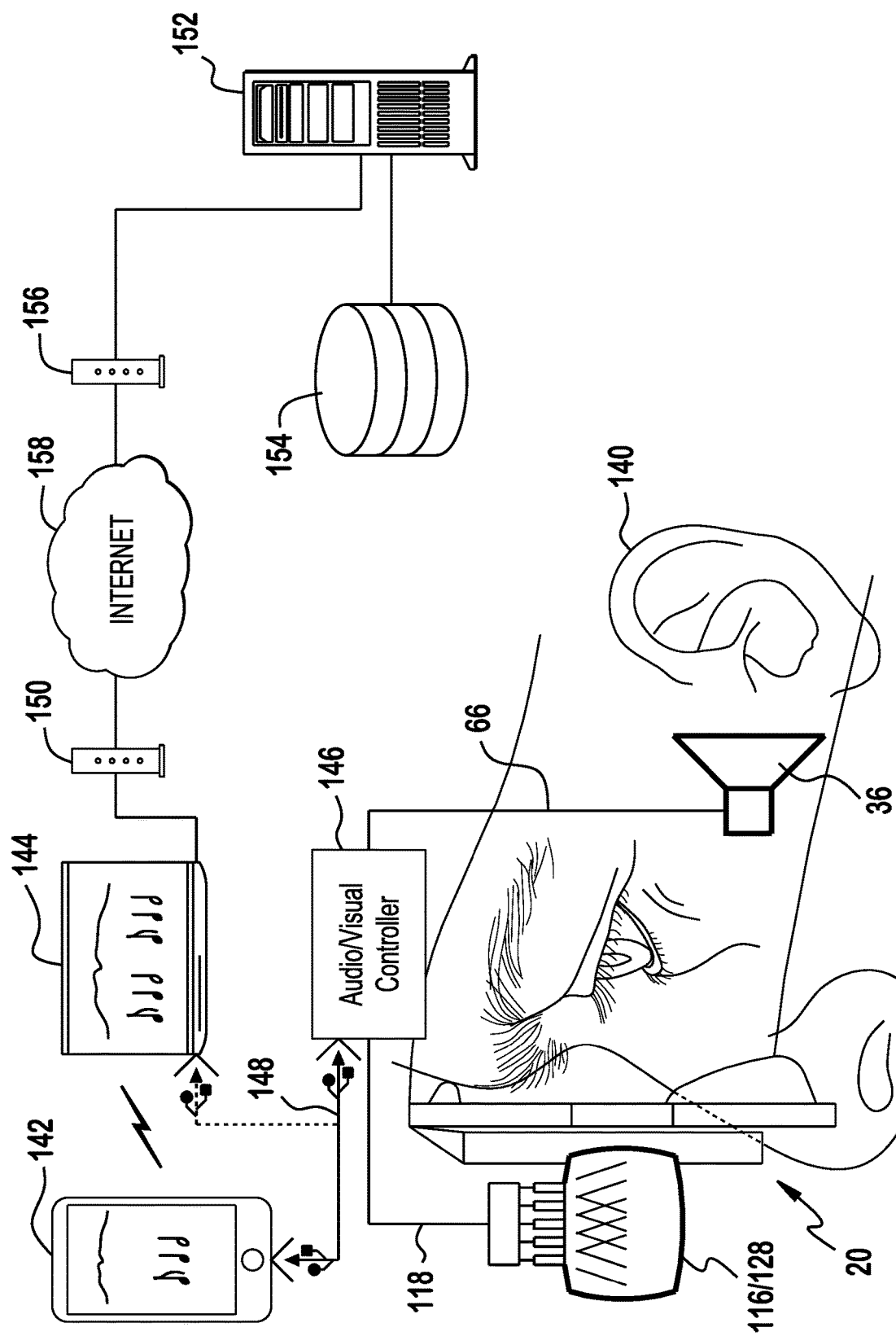
FIG. 14 is a schematic diagram for a system for sensory control which includes the sensory control headgear 20 in which the speaker 36 and the illumination panel 116 are driven by an audio/visual controller 146 that is preferably located on/in the mask body 22. The controller 146 may be connected via USB to mobile devices 142, computers 144, routers 146, 156, the Internet 158, and remote database 154 and servers 152. The illumination panel 116 is shown as a light pipe or illuminating glass, but could be an LCD or video display 128 or any other illuminating device without departing from the scope of the present invention.
Figure 15:
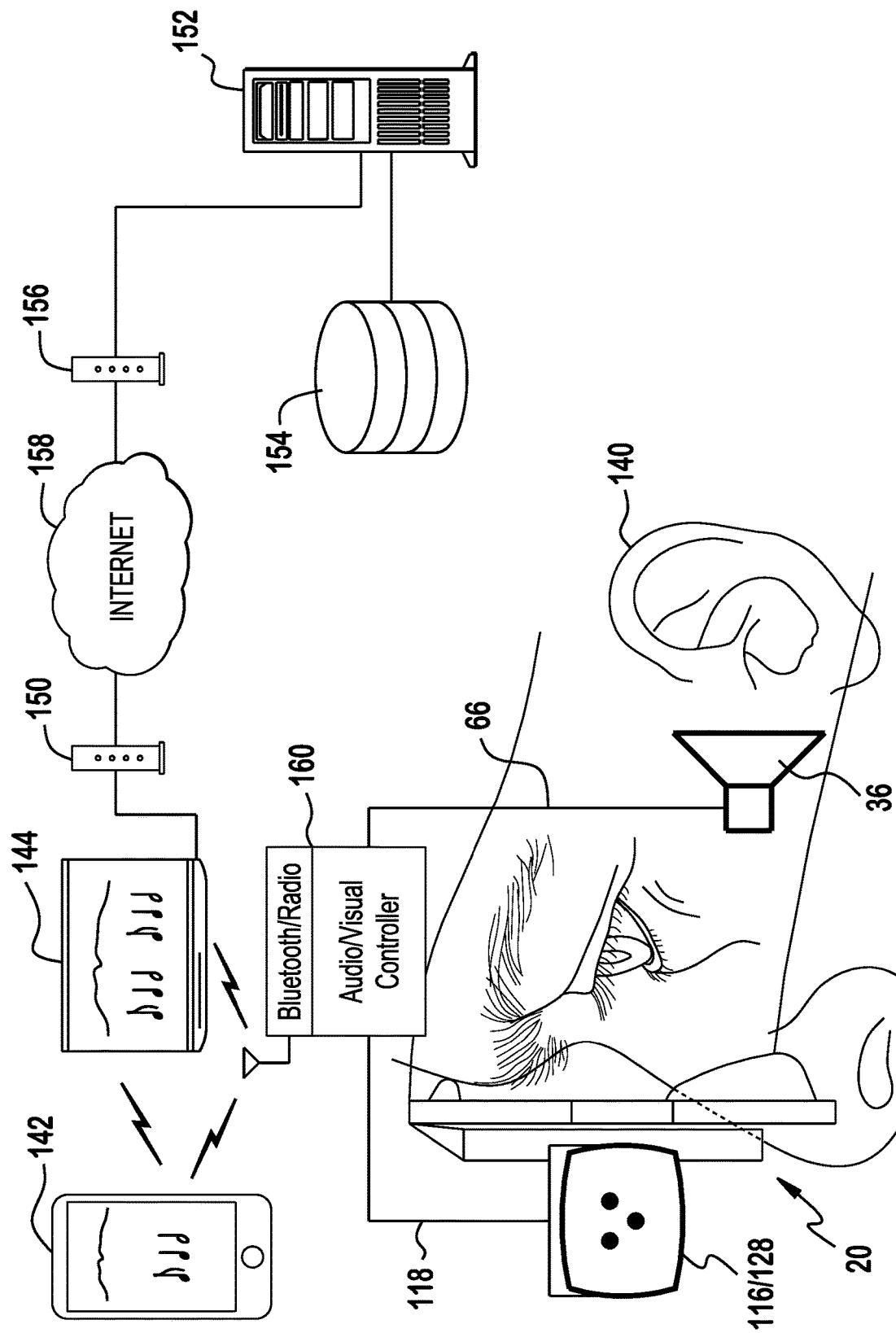
FIG. 15 is schematic diagram for a system for sensory control which preferably includes the sensory control headgear 20 which is similar to that shown in FIG. 14 except for the controller 160 uses Bluetooth or radio signals to connect to various content sources. Additionally, the illumination panel 116, 128 is shown as a video display panel.

Referring to FIGS. 13-15, the sensory control headgear 20 may be part of the sensory control system. The illuminated display 116, 128 which may be disposed within the eye shield 24 such that, when the eye shield 24 is in the second, closed position, the mask body 22 is configured to provide predetermined visual content to the user. The illuminated display 116, 128 is preferably at least one of an illuminating glass panel, an illuminating glass panel, a light pipe lens, a light display, a video display, a liquid crystal display, a light emitting diode display, a multicolor light emitting diode, and a light emitting diode.

The system may work in tandem with a controller located on/in the mask body 22 and may be configured for receiving the predetermined audio content and the predetermined visual content from an external source and then sending the predetermined audio content to the speaker 36 in the mask body 22 and sending the predetermined visual content to an illuminated display 116, 128 disposed within the eye shield 24 such that when the eye shield 24 is in the second, closed position, the mask body 22 is configured to provide the predetermined visual content to the user 21.

It is preferred, but not necessary that the controller receives the predetermined audio content and the predetermined visual content from one at least one of a mobile electronic device, a mobile phone, a laptop, the Internet, a training computer located remotely over the Internet or a local area network. Alternatively, the controller may receive the predetermined audio content and the predetermined visual content from a training computer. The training computer may have a training computer microphone and a training computer speaker, a second microphone being positioned on the mask body to allow the user to communicate with an operator of the training computer to allow a third party to monitor and assist the user.

Referring specifically to FIG. 13, the system for sensory control which preferably includes the sensory control headgear 20 of the present invention may include the speaker 36 connected via adapters and wires 66 two mobile phones and such were mobile electronic devices 142 and computers, including tablets and laptops, 144. Referring specifically to FIG. 14, the controller 146 may be connected via USB to mobile devices 142, computers 144, routers 146, 156, the Internet 158, and remote database 154 and servers 152. The illumination panel 116 is shown as a light pipe or illuminating glass, but could be an LCD or video display 128 or any other illuminating device without departing from the scope of the present invention. Referring specifically to FIG. 15, the controller 160 uses Bluetooth or radio signals to connect to various content sources. Additionally, the illumination panel 116, 128 is shown as a video display panel.

Referring specifically to FIG. 16, the system may include a remotely located computer 164 and headset 166 for use by a trainer. The sensory control headgear 20 preferably includes a microphone 168 to allow for two-way audible communication with the trainer. The trainer can use the headset 166 and the computer display to guide the headgear where are through specific sensory input. This can be used to facilitate meditation, hypnosis, self-healing, etc.

It is recognized by those skilled in the art that changes may be made to the above described sensory control headgear 20 without departing from the broad inventive concept thereof. It is understood, therefore, that this invention is not limited to the particular embodiments disclosed, but is intended to cover all modifications which are within the spirit and scope of the invention as defined by the above specification, the appended claims and/or shown in the attached drawings.

What is claimed is:

1. A sensory control headgear configured for placement over a portion of a head of a user, comprising:
a mask body defining a central body portion and first and second lateral body portions configured for placement over eyes and ears of the user, the mask body being configured to reduce external noise perceived by the user, the mask body having a rear side configured to contact the head of the user when worn and a front side, the mask body defining a plurality of eye holes in the central body portion, the first and second lateral body portions being detachably securable to each other such that the sensory control headgear is configured to be positioned about the head of the user, the mask body being formed entirely of flexible fabric material;
an eye shield pivotably attached to the mask body for movement between a first, open position in which the user can see external surroundings through the plurality of eye holes in the mask body while the sensory control headgear is worn and a second, closed position in which external visual stimulation is eliminated for the user while the sensory control headgear is worn;
the mask body and the eye shield being configured such that pressure is not exerted onto the eyes of the user while the sensory control headgear is worn;
a speaker disposed within the mask body and configured to provide predetermined audio content to the user; and
an illuminated display disposed within the eye shield such that when the eye shield is in the second, closed position, the mask body is configured to provide predetermined visual content to the user.

2. The sensory control headgear of claim 1, wherein the speaker is located within a chamber in the mask body that allows the speaker to be moved axially between at least two positions.

3. The sensory control headgear of claim 1, wherein the mask body is configured as a single elongated member such that a top of the head of the user is not covered while the sensory control headgear is worn.

4. The sensory control headgear of claim 1, wherein the mask body is configured to contact the face of the user around all of each eye socket of a plurality of eyes so as to encircle each eye socket individually.

5. The sensory control headgear of claim 1, wherein the illuminated display is at least one of an illuminating glass panel, an illuminating glass panel, a light pipe lens, a light display, a video display, a liquid crystal display, a light emitting diode display, a multicolor light emitting diode, and a light emitting diode.

6. The sensory control headgear of claim 1, further comprising a first ridge protuberance positioned on the rear side of the mask body and configured to abut a nose of the user.

7. The sensory control headgear of claim 6, further comprising a second ridge protuberance positioned on the rear side of the mask body and configured to abut a forehead of the user such that the mask body is supported in a spaced apart fashion from the head of the user between the first ridge protuberance and the second ridge protuberance.

8. The sensory control headgear of claim 7, wherein the speaker is located within a chamber in the mask body that allows the speaker to be moved axially between at least two positions.

9. The sensory control headgear of claim 6, wherein the eye shield includes a spacer configured such that when the eye shield is in the second, closed position, the spacer is positioned against the entire perimeter of each of a plurality of eye slots in the mask body.

10. The sensory control headgear of claim 9, wherein the mask body includes a pocket on the front side thereof, a digital source being positioned therein to provide at least one of the predetermined audio content and predetermined visual content.

11. A system for sensory control, comprising:
the sensory control headgear of claim 9; and
a controller located disposed on/in the mask body and configured for receiving the predetermined audio content and the predetermined visual content from an external source and sending the predetermined audio content to the speaker in the mask body and sending the predetermined visual content to the illuminated display disposed within the eye shield such that when the eye shield is in the second, closed position, the mask body is configured to provide the predetermined visual content to the user.

12. The system of claim 11, wherein the controller receives the predetermined audio content and the predetermined visual content from at least one of a mobile electronic device, a mobile phone, a laptop, the Internet, a training computer located remotely over the Internet or a local area network.

13. The system of claim 11, wherein the controller receives the predetermined audio content and the predetermined visual content from a training computer, the training computer having a training computer microphone and a training computer speaker, a second microphone being positioned on the mask body to allow the user to communicate with an operator of the training computer to allow a third party to monitor and assist the user.

14. A sensory control headgear configured for placement over a portion of a head of a user, comprising:
a mask body defining a central body portion and first and second lateral body portions configured for placement over eyes and ears of the user, the mask body being configured to reduce external noise perceived by the user, the mask body having a rear side configured to contact the head of the user when worn and a front side, the mask body defining a plurality of eye holes in the central body portion, the first and second lateral body portions being detachably securable to each other such that the sensory control headgear is configured to be positioned about the head of the user, the mask body being formed entirely of flexible fabric material, wherein the mask body is configured as a single elongated member such that a top of the head of the user is not covered while the sensory control headgear is worn;
an eye shield pivotably attached to the mask body for movement between a first, open position in which the user can see external surroundings through the plurality of eye holes in the mask body while the sensory control headgear is worn and a second, closed position in which external visual stimulation is eliminated for the user while the sensory control headgear is worn, wherein the eye shield includes a spacer configured such that when the eye shield is in the second, closed position, the spacer is positioned against an entire perimeter of each of a plurality of eye slots in the mask body;

the mask body and the eye shield being configured such that pressure is not exerted onto the eyes of the user while the sensory control headgear is worn;

a first ridge protuberance positioned on the rear side of the mask body and configured to abut a nose of the user; and a second ridge protuberance positioned on the rear side of the mask body and configured to abut a forehead of the user such that the mask body is supported in a spaced apart fashion from the head of the user between the first ridge protuberance and the second ridge protuberance when the sensory control headgear is worn.

15. A sensory control headgear configured for placement over a portion of a head of a user, comprising:

a mask body defining a central body portion and first and second lateral body portions configured for placement over eyes and ears of the user, the mask body being configured to reduce external noise perceived by the user, the mask body having a rear side configured to contact the head of the user when worn and a front side, the mask body defining a plurality of eye holes in the central body portion, the first and second lateral body portions being detachably securable to each other such that the sensory control headgear is configured to be positioned about the head of the user, the mask body being formed entirely of flexible fabric material, wherein the mask body is configured as a single elongated member such that a top of the head of the user is not covered while the sensory control headgear is worn;

an eye shield pivotably attached to the mask body for movement between a first, open position in which the user can see external surroundings through the plurality of eye holes in the mask body while the sensory control headgear is worn and a second, closed position in which external visual stimulation is eliminated for the user while the sensory control headgear is worn, the eye shield being formed entirely of flexible fabric material, wherein the eye shield incudes a spacer configured such that when the eye shield is in the second, closed position, the spacer is positioned against an entire perimeter of each of a plurality of eye slots in the mask body;

the mask body and the eye shield being configured such that pressure is not exerted onto the eyes of the user while the sensory control headgear is worn;

a first ridge protuberance positioned on the rear side of the mask body and configured to abut a nose of the user; and a second ridge protuberance positioned on the rear side of the mask body and configured to abut a forehead of the user such that the mask body is supported in a spaced apart fashion from the head of the user between the first ridge protuberance and the second ridge protuberance when the sensory control headgear is worn.

\* \* \* \* \*